(12) United States Patent
Lai et al.

(10) Patent No.: US 10,258,953 B2
(45) Date of Patent: Apr. 16, 2019

(54) SYSTEMS AND PROCESSES FOR PRODUCING POLYETHER POLYOLS

(71) Applicant: Covestro LLC, Pittsburgh, PA (US)

(72) Inventors: Jye-Sheng Lai, Houston, TX (US); William D. Wray, Kingwood, TX (US); Robert A. Lenahan, Imperial, PA (US); Jack R. Reese, Coraopolis, PA (US); D. Mark Morrison, Moon Township, PA (US)

(73) Assignee: COVESTRO LLC, Pittsburgh, PA (US)

( * ) Notice: Subject to any disclaimer, the term of this patent is extended or adjusted under 35 U.S.C. 154(b) by 0 days.

(21) Appl. No.: 15/229,657

(22) Filed: Aug. 5, 2016

(65) Prior Publication Data

US 2018/0036704 A1 Feb. 8, 2018

(51) Int. Cl.
| | |
|---|---|
| *B01J 19/00* | (2006.01) |
| *B01J 19/18* | (2006.01) |
| *C07C 41/03* | (2006.01) |
| *C08G 65/26* | (2006.01) |

(52) U.S. Cl.
CPC ........... *B01J 19/0013* (2013.01); *B01J 19/18* (2013.01); *C07C 41/03* (2013.01); *C08G 65/2663* (2013.01); *C08G 65/2696* (2013.01); *B01J 2219/00033* (2013.01); *B01J 2219/00087* (2013.01)

(58) Field of Classification Search
None
See application file for complete search history.

(56) References Cited

U.S. PATENT DOCUMENTS

| | | | |
|---|---|---|---|
| 3,297,412 A * | 1/1967 | Phillips, Jr. | .......... B01J 19/0013 165/299 |
| 3,404,109 A | 10/1968 | Milgrom | |
| 3,427,334 A | 2/1969 | Belner | |
| 3,829,505 A | 8/1974 | Herold | |
| 3,941,849 A | 3/1976 | Herold | |
| 4,477,589 A | 10/1984 | Van Der Hulst et al. | |
| 5,149,885 A * | 9/1992 | Jubin, Jr. | ............. B01J 19/0013 568/564 |
| 5,158,922 A | 10/1992 | Hinney et al. | |
| 5,159,092 A | 10/1992 | Leuteritz | |
| 5,470,813 A | 11/1995 | Le-Khac | |
| 5,482,908 A | 1/1996 | Le-Khac | |
| 5,689,012 A | 11/1997 | Pazos et al. | |
| 5,783,513 A | 7/1998 | Combs et al. | |
| 5,811,595 A | 9/1998 | Ellis | |
| 6,077,978 A | 6/2000 | McDaniel et al. | |
| 6,664,428 B2 | 12/2003 | Ostrowski et al. | |
| 6,673,972 B2 | 1/2004 | Ostrowski et al. | |
| 6,716,788 B2 | 4/2004 | Eleveld et al. | |
| 6,780,813 B1 | 8/2004 | Hofmann et al. | |

(Continued)

FOREIGN PATENT DOCUMENTS

| | | |
|---|---|---|
| EP | 0700949 A2 | 3/1996 |
| EP | 0743093 A1 | 11/1996 |

(Continued)

*Primary Examiner* — Rosalynd A Keys
(74) *Attorney, Agent, or Firm* — Donald R. Palladino

(57) ABSTRACT

Disclosed are processes and systems for producing polyether polyols and for the recovery of heat generated during such polyether polyol production.

10 Claims, 1 Drawing Sheet

(56) References Cited

U.S. PATENT DOCUMENTS

| | | |
|---|---|---|
| 6,835,687 B2 | 12/2004 | Hofmann et al. |
| 7,008,900 B1 | 3/2006 | Hofmann et al. |
| 7,012,164 B2 | 3/2006 | Yamada et al. |
| 7,022,884 B2 | 4/2006 | Ostrowski et al. |
| 7,528,288 B2 | 5/2009 | Ostrowski et al. |
| 7,723,465 B2 | 5/2010 | Herwig et al. |
| 7,750,191 B2 | 7/2010 | Ostrowski et al. |
| 7,803,332 B2 * | 9/2010 | Brown .................. B01J 8/067 422/201 |
| 7,919,575 B2 | 4/2011 | Browne |
| 7,968,754 B2 | 6/2011 | Ostrowski et al. |
| 8,324,325 B2 | 12/2012 | Knott et al. |
| 8,334,355 B2 | 12/2012 | Henning et al. |
| 2003/0073873 A1 | 4/2003 | Jochem Brons et al. |
| 2004/0192801 A1 | 9/2004 | Bauer et al. |
| 2008/0021191 A1 | 1/2008 | Reese et al. |
| 2008/0132728 A1 | 6/2008 | McDaniel et al. |
| 2008/0132729 A1 | 6/2008 | McDaniel et al. |
| 2009/0137752 A1 | 5/2009 | Knott et al. |
| 2010/0266518 A1 | 10/2010 | Springer et al. |
| 2011/0085772 A1 | 4/2011 | Benjamin et al. |
| 2011/0105802 A1 | 5/2011 | Villa et al. |
| 2013/0224078 A1 | 8/2013 | Van Grambezen et al. |
| 2013/0345476 A1 | 12/2013 | Reese |
| 2014/0275633 A1 | 9/2014 | Reese et al. |
| 2016/0107962 A1 * | 4/2016 | Greager .............. C07C 29/1512 518/706 |

FOREIGN PATENT DOCUMENTS

| | | | |
|---|---|---|---|
| EP | 0761708 A2 | 3/1997 | |
| JP | 4145123 A | 5/1992 | |
| WO | 9740086 | 10/1997 | |
| WO | 9816310 | 4/1998 | |
| WO | WO2009143103 A1 * | 11/2009 | ............ G08G 65/00 |
| WO | 2011085772 A1 | 7/2011 | |

* cited by examiner

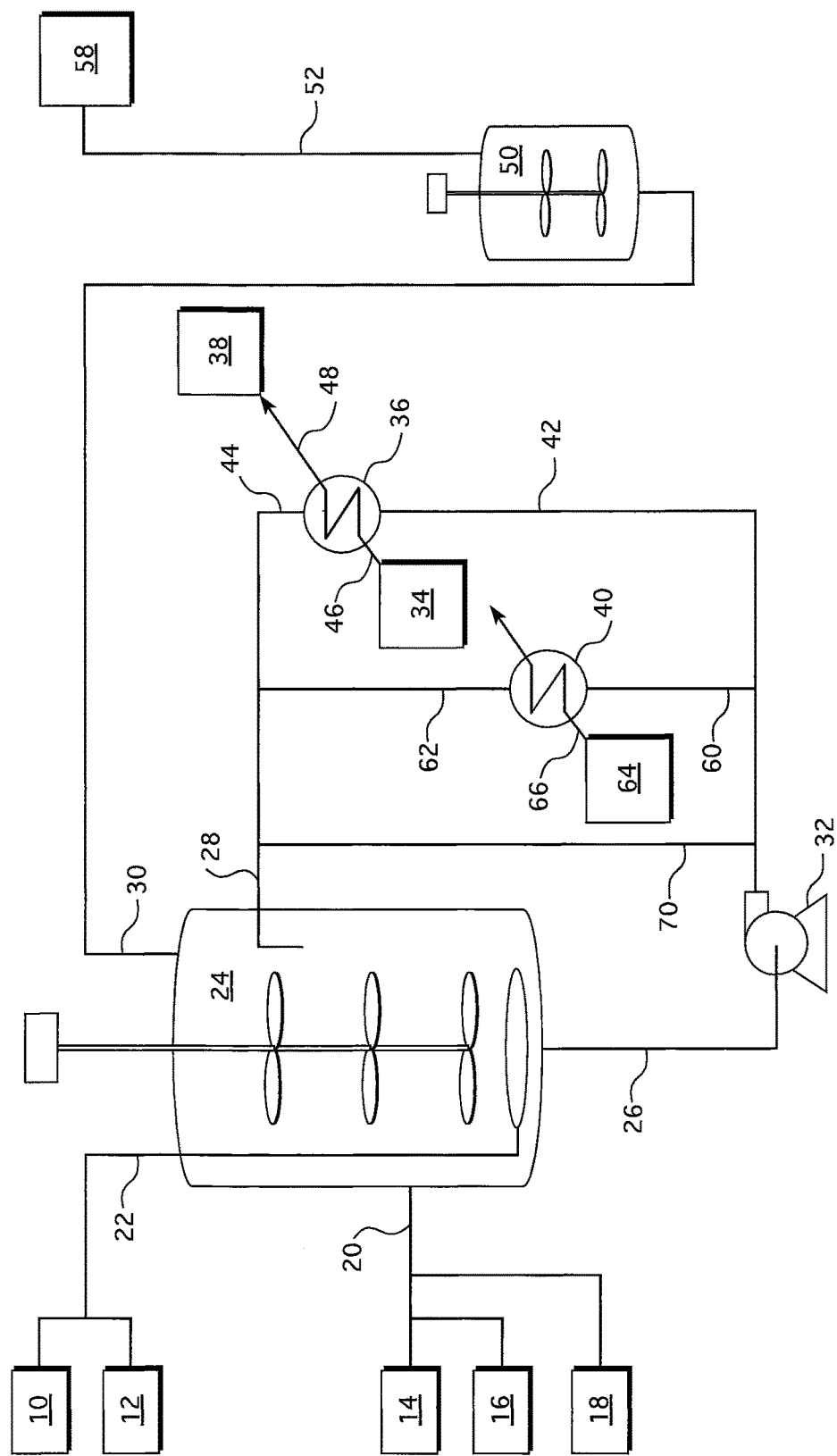

US 10,258,953 B2

SYSTEMS AND PROCESSES FOR PRODUCING POLYETHER POLYOLS

FIELD

The present invention is directed to, among other things, processes and systems for producing polyether polyols.

BACKGROUND

The preparation of polyether polyols by oxyalkylation of an alkylene oxide with a low molecular weight starter compound in the presence of a double metal cyanide (DMC) catalyst is known. Polyether polyols produced by DMC catalysis are often characterized by low unsaturation and low polydispersity (i.e. a narrow molecular weight range), which is particularly desirable in many applications for such polyether polyols, such as in the manufacture of flexible polyurethane foams.

Continuous processes for preparing such polyether polyols using DMC catalysts are also known. In some cases, for example, a continuous stirred tank reactor ("CSTR") is used in which the CSTR is initially charged with a mixture of starter compound and DMC catalyst, the catalyst is activated and additional starter, alkylene oxide and DMC catalyst are continuously added to the CSTR and polyether polyol is continuously removed from the CSTR.

The foregoing oxyalkylation in the presence of a DMC catalyst is an exothermic reaction. As a result, continuous processes for preparing polyether polyols using DMC catalyst, such as those that use a CSTR, can be limited in rate by the heat removal rate of the reactor or heat exchangers in the system. This can limit the capacity of plants that incorporate such processes.

As a result, it would be desirable to provide systems and processes for the production of polyether polyols using DMC catalysis in which the energy created by the exothermic oxyalkylation reaction is efficiently removed from the reactor and is put to beneficial use, while also allowing significantly increased space-time yields, thereby increasing plant capacity, and causing no changes in product quality.

The present invention was made in view of the foregoing.

SUMMARY OF THE INVENTION

In certain respects, the present invention is directed to systems for the recovery of heat generated in the continuous production of a polyether polyol using a double metal cyanide catalyst. These systems comprise: (a) a continuous reactor comprising a recirculation outlet and a product storage outlet; (b) a source of alkylene oxide in fluid communication with an inlet of the continuous reactor; (c) a source of the catalyst in fluid communication with an inlet of the continuous reactor; (d) a source of low molecular weight starter in fluid communication with an inlet of the continuous reactor; and (e) a water-cooled heat exchanger. The water-cooled heat exchanger comprises: (1) a cooling water inlet in fluid communication with a source of cooling water; and (2) a cooling water outlet in fluid communication with a boiler system.

In other respects, the present invention is directed to systems for the continuous production of a polyether polyol using a double metal cyanide catalyst. These systems comprise: (a) a continuous reactor comprising a recirculation outlet and a product storage outlet; (b) a source of alkylene oxide in fluid communication with an inlet of the continuous reactor; (c) a source of the catalyst in fluid communication with an inlet of the continuous reactor; (d) a source of low molecular weight starter in fluid communication with an inlet of the continuous reactor; (e)(i) a first external water-cooled heat exchanger and (e)(ii) a second water-cooled heat exchanger disposed in parallel with the first external water-cooled heat exchanger. In these systems, the first external water-cooled heat exchanger comprises: (1) a polyether polyol inlet in fluid communication with the recirculation outlet of the continuous reactor; (2) a polyether polyol outlet in fluid communication with an inlet of the continuous reactor; and (3) a cooling water inlet in fluid communication with a source of cooling water.

The present invention is also directed to, among other things, processes that utilize such systems and polyether polyols produced by such processes and the use of such polyether polyols in the manufacture of polyurethanes.

BRIEF DESCRIPTION OF THE DRAWINGS

FIG. 1 is a schematic illustration of an embodiment of a system of the present invention which is suitable for carrying out processes of the present invention.

DETAILED DESCRIPTION

Various embodiments are described and illustrated in this specification to provide an overall understanding of the structure, function, properties, and use of the disclosed inventions. It is understood that the various embodiments described and illustrated in this specification are non-limiting and non-exhaustive. Thus, the invention is not limited by the description of the various non-limiting and non-exhaustive embodiments disclosed in this specification. The features and characteristics described in connection with various embodiments may be combined with the features and characteristics of other embodiments. Such modifications and variations are intended to be included within the scope of this specification. As such, the claims may be amended to recite any features or characteristics expressly or inherently described in, or otherwise expressly or inherently supported by, this specification. Further, Applicant(s) reserve the right to amend the claims to affirmatively disclaim features or characteristics that may be present in the prior art. Therefore, any such amendments comply with the requirements of 35 U.S.C. § 112 and 35 U.S.C. § 132(a). The various embodiments disclosed and described in this specification can comprise, consist of, or consist essentially of the features and characteristics as variously described herein.

Any patent, publication, or other disclosure material identified herein is incorporated by reference into this specification in its entirety unless otherwise indicated, but only to the extent that the incorporated material does not conflict with existing definitions, statements, or other disclosure material expressly set forth in this specification. As such, and to the extent necessary, the express disclosure as set forth in this specification supersedes any conflicting material incorporated by reference herein. Any material, or portion thereof, that is said to be incorporated by reference into this specification, but which conflicts with existing definitions, statements, or other disclosure material set forth herein, is only incorporated to the extent that no conflict arises between that incorporated material and the existing disclosure material. Applicant(s) reserves the right to amend this specification to expressly recite any subject matter, or portion thereof, incorporated by reference herein.

In this specification, other than where otherwise indicated, all numerical parameters are to be understood as being prefaced and modified in all instances by the term "about", in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described in the present description should at least be construed in light of the number of reported significant digits and by applying ordinary rounding techniques.

Also, any numerical range recited in this specification is intended to include all sub-ranges of the same numerical precision subsumed within the recited range. For example, a range of "1.0 to 10.0" is intended to include all sub-ranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited in this specification is intended to include all lower numerical limitations subsumed therein and any minimum numerical limitation recited in this specification is intended to include all higher numerical limitations subsumed therein. Accordingly, Applicant(s) reserves the right to amend this specification, including the claims, to expressly recite any sub-range subsumed within the ranges expressly recited herein. All such ranges are intended to be inherently described in this specification such that amending to expressly recite any such sub-ranges would comply with the requirements of 35 U.S.C. § 112 and 35 U.S.C. § 132(a).

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an implementation of the described embodiments. Further, the use of a singular noun includes the plural, and the use of a plural noun includes the singular, unless the context of the usage requires otherwise.

As indicated, in certain embodiments, the present invention is directed to systems for the recovery of heat generated in the continuous production of a polyether polyol using a double metal cyanide catalyst. In certain embodiments, the polyether polyol has a hydroxyl (OH) number of from 10 to 300 mg KOH/gram polyol, such as 28 to 112 mg KOH/gram polyol, 42 to 112 mg KOH/gram polyol, or 42 to 56 mg KOH/gram polyol. The polyether polyol may have an OH number ranging between any combination of these upper and lower values, inclusive, such as, for example from at least 10 to less than or equal to 300 mg KOH/gram polyol, such as 42 to less than or equal to 112 mg KOH/gram polyol. The OH numbers reported herein can be determined, using acetic anhydride, according to ASTM E222-10 or, using phthalic anhydride, according to ASTM D4274-16.

As is known by one skilled in the art, OH numbers of from 10 to 300 mg KOH/gram polyol correspond to equivalent weights of 6000 to 190 Da, respectively; and OH numbers of from 42 to 112 mg KOH/gram polyol correspond to equivalent weights of from 1300 to 500 Da, respectively.

The polyether polyols produced with systems and processes of the present invention, in certain embodiments, have equivalent weights of 200 Da to 6,000 Da, such as 250 Da to 2,000 Da, or, in some cases, 500 Da to 1,300 Da. The polyether polyols may have an equivalent weight ranging between any combination of these values, inclusive of the recited values.

Such polyether polyols may be reacted with one or more isocyanates to provide polyurethane products including, but not limited to, coatings, adhesives, sealants, elastomers, foams, including flexible foams, and the like. Suitable organic polyisocyanates for forming such polyurethanes include unmodified isocyanates, modified polyisocyanates, and isocyanate prepolymers. Such organic polyisocyanates include aliphatic, cycloaliphatic, araliphatic, aromatic, and heterocyclic polyisocyanates of the type described, for example, by W. Siefken in Justus Liebigs Annalen der Chemie, 562, pages 75 to 136. Examples of such isocyanates include those represented by the formula:

in which n is a number from 2-5, such as 2-3, and Q is an aliphatic hydrocarbon group; a cycloaliphatic hydrocarbon group; an araliphatic hydrocarbon group; or an aromatic hydrocarbon group.

Embodiments of the systems and processes of the present invention will now be described with reference to FIG. 1. As is apparent, certain systems of the present invention comprises a continuous reactor 24 comprising a recirculation outlet 26 and a product storage outlet 30. Continuous reactors suitable for use in the present invention can include tubular reactors, flow reactors, loop reactors, or, as is depicted in FIG. 1, continuous stirred tank reactors (CSTR). The continuous reactor 24 is, in certain embodiments, a carbon steel, glass-lined or stainless steel reactor.

As also illustrated in FIG. 1, the systems of the present invention comprise one or more sources of alkylene oxide(s) 10, 12 in fluid communication with an inlet 22 of the continuous reactor 24. Alkylene oxides useful in the present invention include, but are not limited to, ethylene oxide, propylene oxide, 1,2- and 2,3-butylene oxide, isobutylene oxide, epichlorohydrin, cyclohexene oxide, and styrene oxide. In some embodiments, the systems of the present invention comprise a source of propylene oxide 10 and a source of ethylene oxide 12. As illustrated, the ethylene oxide and propylene oxide may be mixed at or prior to reactor inlet 22 and, in some cases, propylene oxide is mixed with ethylene oxide at a weight ratio of at least 85:15, such as at least 90:10. In other embodiments, propylene oxide is used alone. Other alkylene oxides mixed with propylene oxide may also be used.

Embodiments of the systems of the present invention further comprise a source of DMC catalyst 18 in fluid communication with an inlet 20 of the continuous reactor 24. Suitable DMC catalysts include, for example, any crystalline or substantially non-crystalline (i.e. substantially amorphous) DMC catalysts. DMC catalysts suitable for use in the present invention are described, for example, in U.S. Pat. Nos. 3,404,109, 3,829,505, 3,941,849 and 5,158,922. DMC catalysts which are described, for example, in U.S. Pat. No. 5,470,813, EP-A 700 949, EP-A 743 093, EP-A 761 708, WO 97/40086, WO 98/16310 and WO 00/47649 have a very high activity in the homopolymerisation of epoxides and permit the preparation of polyether polyols at very low catalyst concentrations (25 ppm or less), so that separation of the catalyst from the finished product is generally not required. A typical example is the highly active DMC catalysts described in EP-A 700 949, which contain, in addition to a double metal cyanide compound (e.g. zinc hexacyanocobaltate(III)) and an organic complex ligand (e.g. tert-butanol), also a polyether having a number-average molecular weight greater than 500 g/mol.

The preparation of alkaline DMC catalysts, which are suitable for use in the present invention, is described in U.S. Pat. No. 5,783,513. These DMC catalysts have an alkalinity in the range from 0.2 to about 2.0 wt. % as metal oxide based on the mass of metal salt used to prepare the catalyst and are substantially non-crystalline catalysts that result in an improved viscosity and a lower degree of unsaturation in the preparation of polyether polyols from alkylene oxides.

Suitable DMC catalysts are also disclosed in U.S. Pat. No. 6,716,788B2, which describes preparation of alkaline DMC catalysts in the presence of from 0.03 to 0.4 mol of an alkaline metal compound (addition of oxides and/or hydroxides), based on the amount of metal salt used, which is reacted with metal cyanide salt.

In some embodiments, the DMC catalyst used in the systems and process of the present invention is obtained by (i) reacting an aqueous solution of a cyanide-free metal salt with the aqueous solution of a metal cyanide salt in the presence of one or more organic complex ligands, for example in the presence of an ether or alcohol, wherein one or more alkaline metal hydroxides, metal carbonates and/or metal oxides are present either in the aqueous solution of the cyanide-free metal salt, in the aqueous solution of the metal cyanide salt or in both the aqueous solutions and wherein the sum of the alkaline metal hydroxides, metal carbonates and/or metal oxides used is 0.3 to 1.8 mole, such as 0.6 to 1.6 mole, or, in some cases, 0.8 to 1.4 mole base equivalents (based on 1 mole of the metal cyanide salt used for the synthesis of the catalyst), (ii) separating the solid from the suspension obtained from (i) by, for example, centrifugation or filtration, (iii) optionally washing the isolated solid with an aqueous solution of an organic complex ligand, such as by re-suspending the solid and then isolating it again by filtration or centrifugation, (iv) drying the resulting solid, optionally after pulverization, at a temperature of within the range of 20 to 100° C. and at a pressure of from 0.1 mbar to normal pressure (1013 mbar), and wherein in (i) or immediately after the precipitation of the double metal cyanide compound in step (ii), one or more organic complex ligands, often in excess (based on the double metal cyanide compound), and optionally further complex-forming components, are added.

In certain embodiments of the present invention, the double metal cyanide compound(s) contained in the DMC catalyst used in the systems and processes of the present invention are the reaction products of water-soluble cyanide-free metal salts and water-soluble metal cyanide salts, wherein the cyanide-free metal salt, the metal cyanide salt or both the mentioned salts used for the preparation of the DMC catalyst contain(s) 0.3 to 1.8 mole, such as 0.6 to 1.6 mole, or, in some cases, 0.8 to 1.4 mole base equivalents (based on 1 mole of the metal cyanide salt used for the synthesis of the catalyst) in the form of an alkaline metal hydroxide, metal carbonate and/or metal oxide.

For example, in some embodiments, an aqueous solution of zinc chloride (sometimes in excess, based on the metal cyanide salt such as, for example, potassium hexacyanocobaltate) and potassium hexacyanocobaltate are mixed and then dimethoxyethane (glyme) or tert-butanol (sometimes in excess, based on zinc hexacyanocobaltate) is added to the resulting suspension, wherein the potassium hexacyanocobaltate used has previously been mixed with 0.3 to 1.8 mole, such as 0.6 to 1.6 mole, or, in some cases 0.8 to 1.4 mole base equivalents (based on 1 mole of the metal cyanide salt used for the synthesis of the catalyst) of alkaline metal hydroxide, metal carbonate and/or metal oxide.

Cyanide-free metal salts suitable for the preparation of the double metal cyanide compounds often have the general formula $M(X)_n$, in which M is selected from the metal cations $Zn^{2+}$, $Fe^{2+}$, $Ni^{2+}$, $Mn^{2+}$, $Co^{2+}$, $Sr^{2+}$, $Sn^{2+}$, $Pb^{2+}$ and $Cu^{2+}$, each X is an anion, which may be the same or different, such as anions selected from the group of the halides (i.e. fluoride, chloride, bromide, iodide), hydroxide, sulfate, carbonate, cyanate, thiocyanate, isocyanate, isothiocyanate, carboxylate, oxalate and nitrate; n is 1 when X=sulfate, carbonate or oxalate, and n is 2 when X=halide, hydroxide, cyanate, thiocyanate, isocyanate, isothiocyanate or nitrate. In some cases, the cyanide-free metal salts have the general formula $M_r(X)_3$, in which M is selected from the metal cations $Fe^{3+}$, $Al^{3+}$ and $Cr^{3+}$, each X is an anion, which may be the same or different, such as an anion selected from the group of the halides (i.e. fluoride, chloride, bromide, iodide), hydroxide, sulfate, carbonate, cyanate, thiocyanate, isocyanate, isothiocyanate, carboxylate, oxalate and nitrate; r is 2 when X=sulfate, carbonate or oxalate, and r is 1 when X=halide, hydroxide, cyanate, thiocyanate, isocyanate, isothiocyanate, carboxylate or nitrate. In some embodiments, the cyanide-free metal salts have the general formula $M(X)_s$, in which M is selected from the metal cations $Mo^{4+}$, $V^{4+}$ and $W^{4+}$, each X is an anion, which may be the same or different, such as an anion selected from the group of the halides (i.e. fluoride, chloride, bromide, iodide), hydroxide, sulfate, carbonate, cyanate, thiocyanate, isocyanate, isothiocyanate, carboxylate, oxalate and nitrate; s is 2 when X=sulfate, carbonate or oxalate, and s is 4 when X=halide, hydroxide, cyanate, thiocyanate, isocyanate, isothiocyanate, carboxylate or nitrate. In other embodiments, the cyanide-free metal salts have the general formula $M(X)_t$, in which M is selected from the metal cations $Mo^{6+}$ and $W^{6+}$, each X is an anion, which may be the same or different, such as an anion selected from the group of the halides (i.e. fluoride, chloride, bromide, iodide), hydroxide, sulfate, carbonate, cyanate, thiocyanate, isocyanate, isothiocyanate, carboxylate, oxalate and nitrate; t is 3 when X=sulfate, carbonate or oxalate, and t is 6 when X=halide, hydroxide, cyanate, thiocyanate, isocyanate, isothiocyanate, carboxylate or nitrate.

Examples of suitable cyanide-free metal salts are zinc chloride, zinc bromide, zinc iodide, zinc acetate, zinc acetylacetonate, zinc benzoate, zinc nitrate, iron(II) sulfate, iron (II) bromide, iron(II) chloride, cobalt(II) chloride, cobalt(II) thiocyanate, nickel(II) chloride and nickel(II) nitrate. Mixtures of different metal salts can also be used.

Metal cyanide salts suitable for the preparation of the double metal cyanide compounds, in some embodiments, have the general formula $(Y)_aM'(CN)_b(A)_c$, in which M' is selected from one or more metal cations from the group consisting of Fe(II), Fe(III), Co(II), Co(III), Cr(II), Cr(III), Mn(II), Mn(III), Ir(III), Ni(II), Rh(III), Ru(II), V(IV) and V(V), Y is selected from one or more metal cations from the group consisting of alkali metal (i.e. $Li^+$, $Na^+$, $K^+$, $Rb^+$, $Cs^+$) and alkaline earth metal (i.e. $Be^{2+}$, $Ca^{2+}$, $Mg^{2+}$, $Sr^{2+}$, $Ba^{2+}$), A is selected from one or more anions from the group consisting of halides (i.e. fluoride, chloride, bromide, iodide), hydroxide, sulfate, carbonate, cyanate, thiocyanate, isocyanate, isothiocyanate, carboxylate, oxalate or nitrate, and a, b and c are integers, the values for a, b and c being so chosen that the electroneutrality of the metal cyanide salt is given; a is, in some embodiments, 1, 2, 3 or 4; b is, in some embodiments, 4, 5 or 6; and c, in some embodiments, has the value 0.

Specific, but non-limiting, examples of suitable metal cyanide salts are potassium hexacyanocobaltate(III), potassium hexacyanoferrate(II), potassium hexacyanoferrate(III), calcium hexacyanocobaltate(III) and lithium hexacyanocobaltate(III).

In certain embodiments, the double metal cyanide compounds which are contained in the DMC catalysts used in the systems and process of the present invention are compounds of the general formula $M_x[M'_{x'}(CN)_y]_z$, in which M is as defined in the formulae above and M' is as defined in the formula above, and x, x', y and z are integers and are so chosen that the electroneutrality of the double metal cyanide compound is given. In some embodiments, x=3, x'=1, y=6 and z=2, M=Zn(II), Fe(II), Co(II) or Ni(II) and M'=Co(III), Fe(III), Cr(III) or Ir(III).

Specific, but non-limiting, examples of suitable double metal halide compounds a) are zinc hexacyanocobaltate(III), zinc hexacyanoiridate(III), zinc hexacyanoferrate(III) and cobalt(II) hexacyanocobaltate(III). Further examples of suitable double metal cyanide compounds are described in, for example, in U.S. Pat. No. 5,158,922 at column 8, lines 29-66, the cited portion of which being incorporated herein by reference.

In certain embodiments, the alkaline metal hydroxides, carbonates and oxides used for the preparation of DMC catalysts suitable for use in the systems and processes of the present invention are the oxides or hydroxides of metals of groups 1a and 2a of the periodic system of the elements (see, for example, "Handbook of Chemistry and Physics, 63rd Edition"). Specific, but non-limiting, examples of suitable alkaline metal hydroxides, metal oxides and metal carbonates are sodium carbonate, sodium hydroxide, potassium carbonate, potassium hydroxide, calcium oxide, calcium hydroxide, barium hydroxide or barium oxide.

The organic complex ligands added in the preparation of the DMC catalysts are disclosed, for example, in U.S. Pat. No. 5,158,922 at column 6, lines 9 to 65, U.S. Pat. Nos. 3,404,109, 3,829,505, 3,941,849, EP-A 700 949, EP-A 761 708, JP 4 145 123, U.S. Pat. No. 5,470,813, EP-A 743 093 and WO-A 97/40086. For example, there are used as organic complex ligands water-soluble, organic compounds with heteroatoms, such as oxygen, nitrogen, phosphorus or sulfur, which are able to form complexes with the double metal cyanide compound. Suitable organic complex ligands include, without limitation, alcohols, aldehydes, ketones, ethers, esters, amides, ureas, nitriles, sulfides and mixtures thereof. In some cases, the organic complex ligands are aliphatic ethers (such as dimethoxyethane), water-soluble aliphatic alcohols (such as ethanol, isopropanol, n-butanol, isobutanol, sec-butanol, tert-butanol, 2-methyl-3-buten-2-ol and 2-methyl-3-butyn-2-ol), compounds which contain both aliphatic or cycloaliphatic ether groups and aliphatic hydroxyl groups (such as, for example, ethylene glycol mono-tert-butyl ether, diethylene glycol mono-tert-butyl ether, tripropylene glycol monomethyl ether and 3-methyl-3-oxetan-methanol). In some embodiments, the organic complex ligands are selected from one or more compounds from the group consisting of dimethoxyethane, tert-butanol, 2-methyl-3-buten-2-ol, 2-methyl-3-butyn-2-ol, ethylene glycol mono-tert-butyl ether and 3-methyl-3-oxetan-methanol.

In the preparation of the DMC catalysts suitable for use in the systems and processes of the present invention, there are optionally used one or more complex-forming component(s) from the compound classes of the polyethers, polyesters, polycarbonates, polyalkylene glycol sorbitan esters, polyalkylene glycol glycidyl ethers, polyacrylamide, poly(acrylamide-co-acrylic acid), polyacrylic acid, poly(acrylic acid-co-maleic acid), polyacrylonitrile, polyalkyl acrylates, polyalkyl methacrylates, polyvinyl methyl ether, polyvinyl ethyl ether, polyvinyl acetate, polyvinyl alcohol, poly-N-vinylpyrrolidone, poly(N-vinylpyrrolidone-co-acrylic acid), polyvinyl methyl ketone, poly(4-vinylphenol), poly(acrylic acid-co-styrene), oxazoline polymers, polyalkyleneimines, maleic acid and maleic anhydride copolymers, hydroxyethylcellulose and polyacetals, or of the glycidyl ethers, glycosides, carboxylic acid esters of polyhydric alcohols, gallic acids or salts, esters or amides thereof, cyclodextrins, phosphorus compounds, α,β-unsaturated carboxylic acid esters or ionic surface-active compounds.

In the preparation of DMC catalysts suitable for use in the systems and processes of the present invention there are, in some cases, reacted in the first step the aqueous solutions of the metal salt (e.g. zinc chloride), used in stoichiometric excess (at least 50 mole %) based on metal cyanide salt, that is to say at least a molar ratio of cyanide-free metal salt to metal cyanide salt of from 2.25 to 1.00, and of the metal cyanide salt (e.g. potassium hexacyanocobaltate) in the presence of the organic complex ligand (e.g. tert-butanol), wherein one or more alkaline metal hydroxides, metal carbonates and/or metal oxides are present either in the aqueous solution of the cyanide-free metal salt, in the aqueous solution of the metal cyanide salt or in both the aqueous solutions, so that a suspension forms which contains the double metal cyanide compound (e.g. zinc hexacyanocobaltate), water, excess cyanide-free metal salt, and the organic complex ligand.

The organic complex ligand can be present in the aqueous solution of the cyanide-free metal salt and/or of the metal cyanide salt, or it can be added directly to the suspension obtained after precipitation of the double metal cyanide compound. It may be advantageous to mix the aqueous solutions of the cyanide-free metal salt and of the metal cyanide salt, wherein one or more alkaline metal hydroxides, metal carbonates and/or metal oxides are present either in the aqueous solution of the cyanide-free metal salt, in the aqueous solution of the metal cyanide salt or in both the aqueous solutions, and the organic complex ligand with vigorous stirring. Optionally, the suspension formed in the first step is then treated with a further complex-forming component. The complex-forming component may be used in a mixture with water and organic complex ligand. A suitable process for carrying out the first step (i.e. the preparation of the suspension) takes place using a mixing nozzle, such as by using a jet disperser as described in WO-A 01/39883.

In the second step, the solid (i.e. the precursor of the catalyst according to the invention) is isolated from the suspension by known techniques, such as centrifugation or filtration.

In some embodiments, the isolated solid is then washed in a third process step with an aqueous solution of the organic complex ligand (e.g. by being resuspended and then isolated again by filtration or centrifugation). In this manner, water-soluble secondary products, for example, such as potassium chloride, can be removed from the DMC catalyst. In some cases, the amount of organic complex ligand in the aqueous wash solution is from 40 to 80 wt. %, based on the total solution.

Optionally, further complex-forming component, such as in the range from 0.5 to 5 wt. %, based on the total solution, is added to the aqueous wash solution in the third step.

It may additionally be advantageous to wash the isolated solid more than once. In some cases, the solid is washed in a first washing step with an aqueous solution of the unsaturated alcohol (e.g. by being resuspended and then isolated again by filtration or centrifugation) in order thus to remove, for example, water-soluble secondary products, such as potassium chloride, from the DMC catalyst. In some embodiments, the amount of unsaturated alcohol in the aqueous wash solution is from 40 to 80 wt. %, based on the total solution of the first washing step. In the further washing steps, either the first washing step is repeated once or several times, such as from one to three times, or, in some cases, a non-aqueous solution, such as, for example, a mixture or solution of organic complex ligand and further complex-forming component, such as in the range from 0.5 to 5 wt. %, based on the total amount of the wash solution is used as the wash solution and the solid is washed therewith once or several times, such as from one to three times.

The isolated and optionally washed solid is then, optionally after pulverization, dried, often at a temperature of 20 to 100° C. and at pressures of generally from 0.1 mbar to normal pressure (1013 mbar).

One suitable process for isolating DMC catalysts suitable for use in the systems and processes of the present invention from the suspension by filtration, filter cake washing and drying is described in WO-A 01/80994.

Crystalline DMC catalysts suitable for use in the present invention are also described in, for example, U.S. Pat. Nos. 5,158,922, 4,477,589, 3,427,334, 3,941,849 and 5,470,813, the disclosures of which are hereby incorporated by reference. DMC catalysts which exhibit a substantially non-crystalline character (i.e. are substantially amorphous) are described in, for example, U.S. Pat. Nos. 5,482,908 and 5,783,513, the disclosures of which are hereby incorporated by reference. The catalysts disclosed in U.S. Pat. Nos. 5,482,908 and 5,783,513 differ from other DMC catalysts because these catalysts exhibit a substantially non-crystalline morphology. In addition, these catalysts are based on a combination of ligands, such as t-butyl alcohol and a polydentate ligand (polypropylene oxide polyol).

In the systems and processes of the present invention, the DMC catalyst concentration used is chosen to ensure a good control of the polyoxyalkylation reaction under the given reaction conditions. In certain embodiments, therefore, DMC catalyst is supplied from DMC catalyst source 18 to the continuous reactor 24 such that the amount of DMC catalyst is in the range of 10 ppm to 200 ppm, such as 15 ppm to 150 ppm, or, in some cases 20 to 120 ppm, based on the weight of the polyether polyol produced. The DMC catalyst may be present in an amount ranging between any combination of these values, inclusive of the recited values.

In systems of the present invention, at least one source of low molecular weight starter 14, 16 is in fluid communication with an inlet 20 of the continuous reactor 24. As depicted in FIG. 1, starter source(s) 14, 16 and catalyst source 18 are in fluid communication with the same inlet 20 of reactor 24. It will be appreciated, however, that it is also possible that starter source(s) 14, 16 can be in fluid communication with a different inlet to reactor 24 than catalyst source 18, if desired. Suitable low molecular weight starters include compounds which have a functionality of at least 2 up to 8, such as 2 to 6, and which have an equivalent weight of up to 115, such as up to 100. Specific examples of suitable starter compounds include, but are not limited to, $C_3$-$C_5$ monols, ethylene glycol, propylene glycol, 1,3-propanediol, 1,4-butanediol, 1,2-butanediol, 1,3-butanediol, 2,3-butanediol, water, glycerin, sorbitol, etc. Mixtures of monomeric starters or their oxyalkylated oligomers may also be utilized. In certain embodiments, the systems of the present invention comprise a source of glycerin 14 and a source of propylene glycol 16. As illustrated in FIG. 1, the glycerin and/or propylene glycol and/or DMC catalyst may be mixed at or prior to reactor inlet 20 and, in some cases, starter(s) and DMC catalyst are mixed at or prior to the inlet 20 such as where the feed stream entering reactor 24 contains 130 to 2000 ppm DMC catalyst, depending on the final desired product hydroxyl number and the final desired catalyst concentration. In other embodiments, the DMC catalyst addition is such that a $3^{rd}$ stream that contains a DMC catalyst loading of 1 to 2 weight percent is used in the starter. In such a procedure, the $2^{nd}$ stream contains starter and is free of DMC catalyst and a first stream comprises alkylene oxide. In some cases, glycerin is the only starter. The catalyst can be added as a dry powder to the starters and mixed or as a slurry in, for example, polyether polyol. The catalyst can be added in a non-activated state (no prior exposure to alkylene oxide) or in an activated state (previously exposed to alkylene oxide).

As indicated earlier, certain systems of the present invention comprise a water-cooled heat exchanger that comprises: (1) a cooling water inlet in fluid communication with a source of cooling water; and (2) a cooling water outlet in fluid communication with a boiler, optionally via a deaerator. For example, in some embodiments, the water-cooled heat exchanger may be embodied as a cooling water jacket present on continuous reactor 24 in which the cooling water jacket has a cooling water inlet in fluid communication with a cooling water inlet in fluid communication with a source of cooling water and a cooling water outlet in fluid communication with a boiler, optionally via a deaerator.

In the embodiment of the present invention depicted in FIG. 1, the system of the present invention comprises an external water-cooled heat exchanger 36. As used herein, "external" means that the heat exchanger is external to, i.e., separate from, the continuous reactor 24 (in contrast with the aforementioned internal coil and cooling water jacket that is integral to the continuous reactor 24). The external water-cooled heat exchanger 36 comprises: (1) a cooling water inlet 46 in fluid communication with a source of cooling water 34; (2) a cooling water outlet 48 in fluid communication with a boiler system 38; (3) a polyether polyol inlet 42 in fluid communication with the recirculation outlet 26 of the continuous reactor 24; and (4) a polyether polyol outlet 44 in fluid communication with an inlet 28 of the continuous reactor 24. As illustrated in FIG. 1, polyether polyol can be conveyed from recirculation outlet 26 of the continuous reactor 24 to polyether polyol inlet 42 of external water-cooled heat exchanger 36 via, for example, a pump 32.

The exact structure of the heat exchanger 36 is not critical. Suitable such exchangers include shell-and-tube heat exchangers and plate-type heat exchangers, for example.

As illustrated if FIG. 1, certain systems of the present invention are designed so that the cooling water outlet 48 of external water-cooled heat exchanger 36 is in fluid communication with boiler system 38. This can enable for a significant reduction in energy usage for the boiler system 38. In particular, such systems of the present invention put to beneficial use the energy created by the exothermic oxyalkylation reaction involved in the production of polyether polyols using DMC catalysis by using water heated as it passes through heat exchanger 36 as boiler feed water in steam generation. In some embodiments, for example, the temperature of the cooling water at the cooling water inlet 46 of heat exchanger 36 is 25 to 35° C., whereas the temperature of the heated cooling water at the outlet 48 of external water-cooled heat exchanger 36, which is in fluid communication with boiler system 38, is 40 to 85° C.

While in embodiments of the present invention the cooling water outlet 48 is in fluid communication with boiler system 38, it will be appreciated that such outlet 48 could be in fluid communication with other types of processing equipment that would make beneficial use of the energy created by the exothermic oxyalkylation reaction, such equipment could include, for example, a heat exchanger for heating other process streams. In such cases, other materials, such as propylene glycol, could be used as the cooling medium in the process, rather than water.

As indicated previously, in certain embodiments of the systems of the present invention, a second water-cooled heat exchanger 40 is disposed in parallel with a first external water-cooled heat exchanger 36. For example, in some embodiments, the second water-cooled heat exchanger may be embodied as a cooling water jacket present on continuous reactor 24 in which the cooling water jacket has a cooling water inlet in fluid communication with a cooling water inlet in fluid communication with a source of cooling water and a cooling water outlet that may, in certain embodiments, be in fluid communication with a boiler system 38.

In the embodiment depicted in FIG. 1, a second external water-cooled heat exchanger 40 is disposed in parallel with the first external water-cooled heat exchanger 36. It will be appreciated, however, that, if desired, more than one external water-cooled heat exchanger (and/or a cooling water jacket on continuous reactor 24) may be disposed in parallel with the first external water-cooled heat exchanger 36. In these systems of the present invention, the first external water-cooled heat exchanger 36 comprises: (1) a polyether polyol inlet 42 in fluid communication with the recirculation outlet 26 of the continuous reactor 24; (2) a polyether polyol outlet 44 in fluid communication with an inlet 28 of the continuous reactor 24; and (3) a cooling water inlet 46 in fluid communication with a source of cooling water 34. In addition, in the embodiment depicted in FIG. 1, the second external water-cooled heat exchanger 40 comprises: (1) a polyether polyol inlet 60 in fluid communication with the recirculation outlet 26 of the continuous reactor 24; (2) a polyether polyol outlet 62 in fluid communication with an inlet 28 of the continuous reactor 24; and (3) a cooling water inlet 66 in fluid communication with a source of cooling water 64. In the embodiment illustrated in FIG. 1, cooling water sources 64 and 34 are depicted separately. However, in some embodiments of the present invention, the same cooling water source is used for first external water-cooled heat exchanger 36 and the second water-cooled heat exchanger 40. In some of these embodiments of the present invention, the cooling water outlet of at least one of the first external water-cooled heat exchanger 36 and the second water-cooled heat exchanger 40 is in fluid communication with boiler system 38. For example, as shown in FIG. 1, in some cases the cooling water outlet of one water-cooled heat exchanger is in fluid communication with boiler system 38. However, in some embodiments, the cooling water outlet of more than one, in some cases all, water-cooled heat exchangers is in fluid communication with boiler 38.

Although not illustrated, it will be appreciated that, if desired, one or more additional heat exchangers could be disposed in series with heat exchanger 36 and/or heat exchanger 40. In addition, in certain embodiments, a bypass line 70 is disposed in parallel with external water-cooled heat exchanger 36 and/or second heat exchanger 40 and is in fluid communication with the outlet of pump 32 and inlet 28 of continuous reactor 24.

In certain embodiments of the systems of the present invention, a deaerator (not shown in FIG. 1), which is a component of boiler system 38, is in fluid communication with the cooling water outlet of at least one of the first external water-cooled heat exchanger 36 and the second external water-cooled heat exchanger 40 and also in fluid communication with the boiler, so that water passes from the external water-cooled heat exchanger(s) through the deaerator and then to the boiler.

As further illustrated in FIG. 1, continuous reactor 24 comprises a polyether polyol outlet 30 that is in fluid communication with post reactor 50. Post reactor 50 may comprise, for example, a tubular reactor, flow reactor, loop reactor, or, as is depicted in FIG. 1, a continuous stirred tank reactor (CSTR). The post reactor 50 provides additional residence time for reaction of any remaining oxides contained in the polyether polyol flowing out of continuous reactor 24. From post reactor 50, the polyether polyol then is, in certain embodiments, transferred via polyether polyol outlet 52 to stripping and storage unit 58. Polyether polyol stripping is often accomplished by atmospheric and/or vacuum distillation processes, which may be conducted batchwise or continuously. In some cases, before and/or after stripping, the polyether polyol is also filtered prior to storage. In some cases, before and/or after stripping, an additive package of, for example, antioxidants and/or acid (i.e. BHT or equivalent) is continuously added to the polyether polyol.

The present invention is also directed to processes for preparing polyether polyols and/or the recovery of energy produced during the oxyalkylation reaction occurring in the process of preparing a polyether polyol that utilize the systems described in this specification.

The processes of the present invention comprise establishing oxyalkylation conditions in a continuous reactor in the presence of a DMC catalyst. Although it is believed that the term "establishing oxyalkylation conditions" in the context of the present invention is self-explanatory, such conditions are established when the reactor temperature, alkylene oxide pressure, catalyst level, degree of catalyst activation, presence of oxyalkylatable compounds within the reactor, etc., are such that upon addition of unreacted alkylene oxide to the reactor, oxyalkylation takes place. By the term "continuously introducing" with respect to addition of alkylene oxide and starter herein is meant truly continuous, or an incremental addition which provides substantially the same results as continuous addition of these components. The terms "starter" and "initiator" as used herein are the same unless otherwise indicated.

In certain embodiments of the processes of the invention, oxyalkylation conditions are established in the continuous reactor by charging a polyether polyol containing a DMC catalyst to the continuous reactor, in some cases a continuous stirred tank reactor. In certain embodiments, the polyether polyol contains from 20 to 120 ppm of DMC catalyst. In these embodiments, once the polyether polyol containing DMC catalyst has been charged to the reactor, the reactor contents are heated to a temperature of at least 135° C., such as at least 140° C. or, in some cases, a temperature within the range of 135° C. to 190° C., 135° C. to 180° C., 135° C. to 160° C., 135° C. to 150° C. or, in some cases, to a temperature of 140° C. Once the reactor and contents are heated, an initial charge of an alkylene oxide, in some cases propylene oxide, is charged to the reactor over a time period of, for example, 5 to 10 minutes or longer. Within a short time period, i.e., from 5 to 10 minutes, the pressure in the reactor will drop, which indicates that the DMC catalyst has been activated.

Once the DMC catalyst is activated, a feed stream of at least one alkylene oxide, such as propylene oxide, is started and continuously fed to the reactor. In addition, a separate feed stream of low molecular weight starter having a molecular weight of from 50 to 250 is started and continuously fed to the reactor. The feed stream of the low molecular weight starter also, in some cases, contains DMC catalyst in an amount of, for example, from 130 to 2000 ppm, depending on the final product hydroxyl number and the final desired catalyst concentration. An alternative method for the catalyst addition is to have a 3rd stream that contains a catalyst loading of 1 to 2 weight % in either the low molecular weight starter or a low molecular weight polyether. In this method, the 2nd stream contains low molecular weight starter and is free of DMC catalyst; and the 1st stream comprises the alkylene oxide.

Oxyalkylation occurs in the reactor at a temperature that is sufficient to prevent deactivation of the DMC catalyst. In certain embodiments, this temperature is at least 135° C., such as at least 140° C., or, in some cases, 135° C. to 190° C., 180° C., 135° C. to 160° C., or 135° C. to 150° C. The oxyalkylation reaction continues for 4 residence times or more, such as 6 residence times or more, while maintaining a positive temperature differential between the reaction temperature and the temperature of the cooling/heating loop thus indicating an exothermic reaction that requires cooling. In some embodiments, during the oxyalkyation, the concentration of unreacted alkylene oxide in the contents of the continuous reactor is maintained at a level of from 1 to 3%, such as 1 to 2%, by weight, based on the total weight of the contents in the reactor, and/or the hydroxyl number of the reactor contents is maintained in the range of 10 to 300 mg KOH/gram polyol, such as 28 to 112 mg KOH/gram polyol, 42 to 112 mg KOH/gram polyol, or 42 to 56 mg KOH/gram polyol.

In the processes of the present invention, removal of the partially oxyalkylated polyether polyol from the continuous oxyalkylation reactor is continuous. The temperature at which the partially oxyalkylated polyether polyol further reacts can increase during this step due to the exothermic reaction of the residual alkylene oxide onto the end of the polymer chains. Minimal or no external cooling is typically applied at this point in the process. In addition, it is not typically necessary to heat this portion of the process due to the exothermic nature of the polymerization reaction that occurs. In general, the temperature of the reaction mixture entering this step of the process is at least 140° C., such as at least 160° C., such as 140° C. or 160° C. to 220° C., 140° C. or 160° C. to 200° C., or, in some cases, 140° C. or 160° C. to 185° C.

In addition, the reaction mixture may increase in temperature by up to 35° C. as a result of the exothermic polymerization. Generally, however, the temperature increase of this reaction mixture is more typically from 10° C. to 25° C.

In certain embodiments, the partially completed (i.e. oxyalkylated) polyether polyol is continuously removed from the full liquid reactor through a back pressure regulator. The partially oxyalkylated polyether polyol is allowed to further react, such as in post reactor 50, until the unreacted alkylene oxide content of the reaction mixture is reduced to 0.001% or less, such as 0.0005% or less, by weight. In some embodiments, the final product contains small amounts of catalyst residues, i.e., less than or equal to 100 ppm, such as less than or equal to 50 ppm; small quantities of the initiator compound or low molecular weight alkoxylates thereof; and small amounts of other organic impurities and water. As is known in the production of polyoxyalkylated polyether polyols, volatile compounds can be flashed or stripped from the polyols, and catalyst residues may remain in the product or may be removed. Moisture can be removed by stripping the polyols, as described above.

The minimum build ratios for the continuous oxyalkylation reactor are, in some embodiments, at least 6, such as at least 6.5, at least 7, or, in some cases, at least 8. The maximum build ratios for the continuous oxyalkylation reactor are, in some embodiments, less than or equal to 180, such as less than or equal to 65, or, in some embodiments, less than or equal to 33. The build ratios for the continuous oxyalkylation reactor may, for example, be 6 to 180, 6.5 to 65, or, in some cases, 8 to 33. These same build ratios are also suitable for the overall process. In some embodiments, a build ratio of 8 to 33 is used when glycerin is the low molecular weight starter. Another suitable build ratio is 7 to 180.

In some embodiments, the low molecular weight starter is acidified with a small amount of a suitable acid as described in, for example, U.S. Pat. Nos. 6,077,978 and 7,919,575, the disclosures of which are herein incorporated by reference. The acid may be any inorganic protic mineral acid or organic acid. In certain embodiments, the amount of acid to be added to the low molecular weight starter is 30 to 200 ppm, such as 30 to 100 ppm, based on the weight of the low molecular weight starter. In some embodiments, phosphoric acid is the acid that is used.

In some embodiments, when using a 3rd stream containing an acidified low molecular weight starter or polyol as the catalyst carrier, the acid level in the mixture of carrier and catalyst is less than 1500 ppm, such as less than 1250 ppm.

As used herein, the term "partially", with regard to the oxyalkylated polyether polyols formed, means that the oxyalkylation of the starter to form the polyether polyol is substantially completed. In other words, after the oxyalkylated polyether polyol is recovered or removed from the continuous oxyalkylation reactor, a minor amount of reaction occurs outside of the reactor. More specifically, at the point the oxyalkylated polyether polyol is recovered from the continuous oxyalkylation reactor, the reaction is at least 98% complete, at least 98.5% complete, or, in some cases, at least 99% complete.

In certain embodiments of the processes of the present invention, heat is continuously removed from the polyether polyol by utilizing a water-cooled heat exchanger. Suitable water-cooled heat exchangers include a water-cooled jacket disposed on the continuous reactor. In the embodiment depicted in FIG. 1, however, the polyether polyol is recirculated from a recirculation outlet of the continuous reactor to an inlet of the continuous reactor via a recirculation outlet of an external water-cooled heat exchanger. In some embodiments, as evidenced by FIG. 1, such recirculation is accomplished by means of a pump 32. Moreover, in certain embodiments of the processes of the present invention heated cooling water from the external water-cooled heat exchanger is fed to a boiler system 38. Such processes enable a significant reduction in energy usage for the boiler system 38. In particular, such processes of the present invention put to beneficial use the energy created by the continuous exothermic oxyalkylation reaction involved in the production of polyether polyols using DMC catalysis by using water heated as it passes through heat exchanger 36 as boiler feed water in steam generation. In some embodiments, for example, the temperature of the cooling water at the cooling water inlet 46 of heat exchanger 36 is 25 to 35° C., whereas the temperature of the heated cooling water at the outlet 48 of external water-cooled heat exchanger 36, which is in fluid communication with boiler system 38, is 40 to 85° C.

In certain embodiment of the processes of the present invention, heated cooling water is fed from the external water-cooled heat exchanger 36 to the boiler system 38, which may include a deaerator (not shown).

Moreover, in certain embodiments of the processes of the present invention, heat is continuously removed from the polyether polyol by recirculating polyether polyol from an outlet of the continuous reactor to an inlet of the continuous reactor by passing a first portion of polyether polyol through a first external water-cooled heat exchanger and in parallel passing a second portion of polyether polyol through a second external water-cooled heat exchanger disposed in parallel with the first heat exchanger. Such a process is evidenced by FIG. 1.

In certain embodiments, at least 50% by weight, such as at least 60% by weight, of polyether polyol is passed through the first external water-cooled heat exchanger and the remainder is passed through the second external water-cooled heat exchanger.

In certain embodiments, the process of the present invention have a space-time yield of at least 500 kg/m$^3$*hr, such as at least 600 kg/m$^3$*hr.

There are several advantages of the systems and processes of the present invention. These include: (a) utilization of a continuous process for the production of polyether polyols that allows for a significant reduction in energy usage for plant steam generation as water that is continuously heated as it passes through heat exchanger(s) is used as boiler feed water; (b) enablement of significantly increased (increases of 20% or more, in some cases 30% or more) space-time yields (defined as mass of product per unit time and reactor volume), due to additional cooling capacity through the use of at least two external water-cooled heat exchangers; (c) greater flexibility in operating rates (low and high demand) by varying the amount of product passing through each external heat exchanger and a bypass stream which allows the systems and processes to run at reduced rates while minimizing fouling of the external heat exchangers; and (d) adjustable bias controlling the split of product passing through each external heat exchanger allows operations to maximize heat recovery when possible or continue to run with reduced recovery in times of limited boiler feed water demand. The systems and processes of the present invention do not affect the properties or performance of polyether polyols produced.

The non-limiting and non-exhaustive examples that follow are intended to further describe various non-limiting and non-exhaustive embodiments without restricting the scope of the embodiments described in this specification.

EXAMPLES

Inventive Example 1

Using a commercial scale continuous polyether polyol reactor system as shown in FIG. 1, a polyether polyol was continuously produced that contained 89.4 weight % (based on the final product weight) propylene oxide, 7.4 weight % ethylene oxide, 2.7 weight % glycerin, 0.5 weight % propylene glycol and 20 ppm DMC catalyst as described in U.S. Pat. No. 5,482,908 or Arcol Catalyst 3. The space time yield was 653 kg/m$^3$*hr and the reaction temperature was 140° C. The inlet water temperature to heat exchanger 40 was 30° C. and the outlet temperature was 52° C. and the inlet water temperature to heat exchanger 36 was 30° C. and the outlet temperature was 75° C. The water from the outlet of heat exchanger 36 proceeded via 48 to a boiler system 38 that include a deaerator prior to a boiler where the water was used as boiler feed water. The energy removed from the heat of reaction and hence, recovered or saved in heating the boiler feed water, in heat exchanger 36 was 21 MMBTU/hr (22 GJ/hr). The continuously made polyether polyol had a hydroxyl number of 56 mg KOH/gram polyol and a viscosity of 580 cst @ 25° C.

Inventive Example 2

Using a commercial scale continuous polyether polyol reactor system as shown in FIG. 1, a polyether polyol was continuously produced that contained 96.2 weight % (based on the final product weight) propylene oxide, 3.8 weight % propylene glycol, and 30 ppm DMC catalyst as described in U.S. Pat. No. 5,482,908 or Arcol Catalyst 3. The space time yield was 505 kg/m$^3$*hr and the reaction temperature was 130° C. The inlet water temperature to heat exchanger 40 was 31° C. and the outlet temperature was 41° C. and the inlet water temperature to heat exchanger 36 was 24° C. and the outlet temperature was 48° C. The water from the outlet of heat exchanger 36 proceeded via 48 to a boiler system 38 that include a deaerator prior to a boiler where the water was used as boiler feed water. The energy removed from the heat of reaction and hence, recovered or saved in heating the boiler feed water, in heat exchanger 36 was 15 MMBTU/hr (15.8 GJ/hr). The continuously made polyether polyol had a hydroxyl number of 56 mg KOH/gram polyol and a viscosity of 380 cst @ 25° C.

Comparative Example

Using a commercial scale continuous polyether polyol reactor system as shown in FIG. 1 but with only heat exchanger 40, a polyether polyol was continuously produced that contained 89.4 weight % (based on the final product weight) propylene oxide, 7.4 weight % ethylene oxide, 2.7 weight % glycerin, 0.5 weight % propylene glycol and 20 ppm DMC catalyst as described in U.S. Pat. No. 5,482,908 or Arcol Catalyst 3. The space time yield was 490 kg/m$^3$*hr and the reaction temperature was 140° C. The inlet water temperature to heat exchanger 40 was 30° C. and the outlet temperature was 52° C. The water from the outlet of heat exchanger 40 proceeded to a cooling tower where the heat was released to the atmosphere at a rate of 26 MMBTU/hr (27.5 GJ/hr) and the water is returned to the inlet of heat exchanger 40 via line 66 at 30° C. The continuously made polyether polyol has a hydroxyl number of 56 mg KOH/gram and a viscosity of 580 cst @ 25° C.

What is claimed is:

1. A process for the continuous production of a polyether polyol using a double metal cyanide catalyst and for the recovery of heat generated during the production, comprising:
    (a) establishing oxyalkylation conditions in a continuous reactor in the presence of the catalyst, wherein the continuous reactor comprises a recirculation outlet that is in fluid communication with an external water-cooled heat exchanger;

(b) continuously introducing alkylene oxide and a low molecular weight starter into the continuous reactor to form the polyether polyol;
(c) continuously removing polyether polyol from the continuous reactor via the recirculation outlet;
(d) continuously removing heat from the polyether polyol by recirculating polyether polyol from the recirculation outlet to an inlet of the continuous reactor via a recirculation outlet of the external water-cooled heat exchanger, wherein the external water-cooled heat exchanger comprises;
   (1) a cooling water inlet in fluid communication with a source of cooling water; and
   (2) a cooling water outlet in fluid communication with a boiler system that is not the continuous reactor; and
(e) feeding heated cooling water having a temperature of 40° C. to 85° C. as it exits the water-cooled heat exchanger via the cooling water outlet to the boiler system for use in the generation of steam.

2. The process of claim 1, wherein the polyether polyol recirculating comprises passing a first portion of polyether polyol through a first external water-cooled heat exchanger and in parallel passing a second portion of polyether polyol through a second external water-cooled heat exchanger disposed in parallel with the first external water-cooled heat exchanger, wherein:
   (i) the first external water-cooled heat exchanger comprises:
      (1) a polyether polyol inlet in fluid communication with the recirculation outlet of the continuous reactor;
      (2) a polyether polyol outlet in fluid communication with the inlet of the continuous reactor;
      (3) a cooling water inlet in fluid communication with a source of cooling water; and
      (4) a cooling water outlet; and
   (ii) the second external water-cooled heat exchanger disposed in parallel with the first external water-cooled heat exchanger comprises:
      (1) a polyether polyol inlet in fluid communication with the recirculation outlet of the continuous reactor;
      (2) a polyether polyol outlet in fluid communication with the inlet of the continuous reactor; and
      (3) a cooling water inlet in fluid communication with a source of cooling water; and
      (4) a cooling water outlet,
   wherein the cooling water outlet of at least one of the first external water-cooled heat exchanger and the second water-cooled heat exchanger is in fluid communication with the boiler system that is not the continuous reactor, and
   wherein the process comprises feeding heated cooling water having a temperature of 40° C. to 85° C. as it exits the water-cooled heat exchanger via the cooling water outlet of at least one of the first external water-cooled heat exchanger and the second external water-cooled heat exchanger to the boiler system for use in the generation of steam.

3. The process of claim 2, further comprising feeding heated cooling water through a deaerator that is in fluid communication with the cooling water outlet of at least one of the first external water-cooled heat exchanger and the second external water-cooled heat exchanger and in fluid communication with a boiler.

4. The process of claim 1, wherein the continuous reactor is a continuous stirred tank reactor.

5. The process of claim 1, wherein the process has a space-time yield of at least 500 kg/m3*hr.

6. A process for the continuous production of a polyether polyol using a double metal cyanide catalyst, comprising:
   (a) establishing oxyalkylation conditions in a continuous reactor in the presence of the catalyst, wherein the continuous reactor comprises a recirculation inlet and a recirculation outlet that is in fluid communication with an external water-cooled heat exchanger system, wherein the external water-cooled heat exchanger system comprises;
      (i) a first external water-cooled heat exchanger, comprising:
         (1) a polyether polyol inlet in fluid communication with the recirculation outlet;
         (2) a polyether polyol outlet in fluid communication with the recirculation inlet;
         (3) a cooling water inlet in fluid communication with a source of cooling water; and
         (4) a cooling water outlet; and
      (ii) a second external water-cooled heat exchanger disposed in parallel with the first external water-cooled heat exchanger, comprising:
         (1) a polyether polyol inlet in fluid communication with the recirculation outlet;
         (2) a polyether polyol outlet in fluid communication with the recirculation inlet; and
         (3) a cooling water inlet in fluid communication with a source of cooling water; and
         (4) a cooling water outlet,
   (b) continuously introducing alkylene oxide and a low molecular weight starter into the continuous reactor to form the polyether polyol;
   (c) continuously removing polyether polyol from the continuous reactor via the recirculation outlet; and
   (d) continuously removing heat from the polyether polyol by recirculating polyether polyol from the recirculation outlet to the recirculation inlet by passing a first portion of polyether polyol through the first external water-cooled heat exchanger and in parallel passing a second portion of polyether polyol through the second external water-cooled heat exchanger disposed in parallel with the first external water-cooled heat exchanger.

7. The process of claim 6, wherein the cooling water outlet of at least one of the first external water-cooled heat exchanger and the second water-cooled heat exchanger is in fluid communication with a boiler system that is not the continuous reactor, and the process comprises feeding heated cooling water having a temperature of 40° C. to 85° C. as it exits the water-cooled heat exchanger to the boiler system via the cooling water outlet of at least one of the first external water-cooled heat exchanger and the second external water-cooled heat exchanger for use in the generation of steam.

8. The process of claim 7, further comprising feeding heated cooling water through a deaerator that is in fluid communication with the cooling water outlet of at least one of the first external water-cooled heat exchanger and the second external water-cooled heat exchanger and in fluid communication with a boiler.

9. The process of claim 6, wherein the continuous reactor is a continuous stirred tank reactor.

10. The process of claim 6, wherein the process has a space-time yield of at least 500 kg/m3*hr.

* * * * *